(12) United States Patent
Koverech et al.

(10) Patent No.: US 7,956,091 B2
(45) Date of Patent: Jun. 7, 2011

(54) USE OF CARNITINES FOR THE PREVENTION AND/OR TREATMENT OF DISORDERS CAUSED BY THE ANDROPAUSE

(75) Inventors: Aleardo Koverech, Rome (IT); Giorgio Cavallini, Rome (IT); Giulio Biagiotti, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 601 days.

(21) Appl. No.: 10/535,509

(22) PCT Filed: Nov. 20, 2003

(86) PCT No.: PCT/IT03/00757
§ 371 (c)(1),
(2), (4) Date: May 18, 2005

(87) PCT Pub. No.: WO2004/054567
PCT Pub. Date: Jul. 1, 2004

(65) Prior Publication Data
US 2006/0135606 A1 Jun. 22, 2006

(30) Foreign Application Priority Data
Dec. 13, 2002 (IT) .............................. RM2002A0620

(51) Int. Cl.
*A01N 37/02* (2006.01)
*A01N 43/04* (2006.01)
*A01N 43/60* (2006.01)

(52) U.S. Cl. ........................... 514/550; 514/23; 514/251

(58) Field of Classification Search .................. 514/613
See application file for complete search history.

(56) References Cited

U.S. PATENT DOCUMENTS

| 3,830,931 A * | 8/1974 | Felice | 514/561 |
| 4,474,812 A * | 10/1984 | Cavazza | 514/556 |
| 6,037,373 A * | 3/2000 | De Simone | 514/556 |
| 6,245,378 B1 * | 6/2001 | Cavazza | 426/656 |
| 6,399,116 B1 * | 6/2002 | Xiu | 424/773 |

FOREIGN PATENT DOCUMENTS

EP 0 681 839 A 11/1995

OTHER PUBLICATIONS iHerb.com, Carnitine, http://healthlibrary.epnet.com, copyright 1997, printed pp. 1-13, especially p. 5.*
Tan, Robert State of the Art Anti-Aging Practice: Diagnostic Difficulties of the Andropause (copyright 2003), Associate Professor, Department of Family Medicine at the University of Texas/ Houston, pp. 473-482, (abstract, p. 473).*
G. Cavallini et al., "Oral Propionyl-L-Carnitine and Intraplaque Verapamil in the Therapy of Advanced and Resistant Reyronie's Disease", BJU International, Blackwell Science, vol. 89, No. 9, Jun. 2002, pp. 895-900, XP001146228.
G. Biagiotti et al., "Acetyl-L-Carnitine Vs Tamoxifen in the Oral Therapy of Peyronie's Disease: A Preliminary Report", BJU International, Blackwell Science, vol. 88, No. 1, Jul. 2001, pp. 63-67, XP001106370.

* cited by examiner

*Primary Examiner* — Sreeni Padmanabhan
*Assistant Examiner* — Timothy E Betton
(74) *Attorney, Agent, or Firm* — Lucas & Mercanti, LLP

(57) ABSTRACT

The use of propionyl L-carnitine in combination with acetyl L-carnitine, or one of their pharmaceutically acceptable salts, is disclosed for the preparation of a medicament, or of a nutritional supplement, for the prevention and/or treatment of the disorders of the male andropause caused by ageing or by chemical or surgical castration.

8 Claims, No Drawings

USE OF CARNITINES FOR THE PREVENTION AND/OR TREATMENT OF DISORDERS CAUSED BY THE ANDROPAUSE

This application is the US national phase of international application PCT/IT2003/000575 filed 20 Nov. 2003, which designated the U.S. and claims priority of IT RM2002A000620, filed 13 Dec. 2002, the entire contents of each of which are hereby incorporated by reference.

The invention described herein relates to the use of acetyl L-carnitine and propionyl L-carnitine in combination for the preparation of a medicament for the prevention and/or treatment of disorders caused by the andropause.

Approximately 20% of males over 50 years of age suffer from reduced libido or sexual drive and erectile function, also during the night, depression of mood, and lowering of intellectual activity, and spatial orientation capacity, as well as fatigue, irritability, reduced lean body mass, muscular capacity, mental concentration, and functioning of the hair-growing apparatus, increased visceral fat, atrophy of the skin, and reduced bone density resulting in osteopenia and osteoporosis. This syndrome has been named "androgen decline in the aging male" (ADAM) or "partial androgen deficiency of the aging male" (PADAM) or "andropause" (*The Aging Male,* 4: 151-162, 2001).

In *J. Urol.,* 151: 54-61, 1994 it was reported that this syndrome is due to partly modifiable age-related phenomena.

In this connection, age-related diseases are an expanding field of application owing to the rapid increase in the population aged over 60 (*J. Urol.,* 163: 705-712, 2000).

It is claimed in several quarters that the andropause is associated with a progressive decrease in androgen production (*The Aging Male,* 4: 151-162, 2001) and that androgen replacement therapy may be appropriately used, in the same way that oestrogen replacement therapy has been used for women in the menopause. The symptoms of andropause, in fact, are similar, though less marked, to those resulting from chemical or surgical castration for the treatment of adenocarcinoma of the prostrate (*J. Urol.,* 167: 2361-2368, 2002).

Useful drugs for the treatment of andropause are already known. In *The Aging Male,* 4: 151-162, 2001 it is reported that patients in the andropause obtain a fair amount of benefit if treated with 40×2 mg/day of testosterone undecanoate.

Hormone treatment for andropause is not without its drawbacks; in *J. Urol.,* 151: 54-61, 1994, and in *J. Urol.,* 163: 705-712, 2000, in fact, it is reported that testosterone treatment cannot be given in the presence of asymptomatic or frank prostate cancer.

In *J. Impot. Res.,* 2002 February; 14 Suppl. 1:S93-8 it is reported that the administration of androgens may have adverse effects on the liver, on lipid status, on cardiovascular and prostate diseases, and on sleep and behavioural disorders.

Moreover, in view of the frequency of adenoma and adenocarcinoma (Rigatti P., Scattoni V., *PSA: Antigene prostatico specifico. Edizioni Medico Scientifiche (EDIMES)* Pavia, 1997) it has been found that approximately 30% of patients with symptoms attributable to the andropause cannot be submitted to androgen replacement therapy.

Previous uses of propionyl L-carnitine and acetyl L-carnitine are already known.

In U.S. Pat. No. 5,811,457 the use of propionyl L-carnitine for the treatment of chronic obliterating arteriopathy is described.

In U.S. Pat. No. 6,063,820, the use of alkanoyl L-carnitines is described for the preparation of a therapeutic nutrient compound for subjects suffering from diabetes mellitus.

In European Patent EP 0 973 415, a composition is described consisting of L-carnitine, acetyl L-carnitine and propionyl L-carnitine, useful for athletes subjected to intense physical effort, or for asthenic individuals.

In patent application WO99/17623, a dietetic composition is described, consisting of L-carnitine, acetyl L-carnitine and propionyl L-carnitine for the treatment of alcohol withdrawal syndrome.

In U.S. Pat. No. 6,090,848, it is reported that the combination of L-carnitine and acetyl L-carnitine is useful for the treatment of oligoasthenoteratospermia.

In the medical field there is a strongly perceived need for new therapeutic agents useful for the prevention and/or treatment of disorders of the andropause caused by ageing and by chemical or surgical castration, which do not present the drawbacks associated with the abovementioned drugs known to be useful in this field.

It has now been found that the combination of propionyl L-carnitine and acetyl L-carnitine, or one of their pharmaceutically acceptable salts proves to possess a surprising curative effect on the disorders caused by the andropause.

The combination according to the invention does not present the side effects of the androgens described above, and can also be used in the group of patients who cannot be treated with the above-mentioned androgens.

One object of the present invention then is the use of propionyl L-carnitine in combination with acetyl L-carnitine, or one of their pharmaceutically acceptable salts for the preparation of a medicament for the prevention and/or treatment of andropause symptoms caused by male ageing or by chemical or surgical castration, characterised by the following symptoms: reduced libido or sexual drive and erectile function, also during the night, depression of mood and lowering of intellectual activity and spatial orientation capacity, fatigue, irritability, reduced lean body mass, muscular capacity, mental concentration, and functioning of the hair-growing apparatus, increased visceral fat, atrophy of the skin, and reduced bone density resulting in osteopenia and osteoporosis.

As mentioned above, the andropause is also defined as "androgen decline in the aging male" (ADAM), or "partial androgen deficiency of the aging male" (PADAM).

What is meant by a pharmaceutically acceptable salt of propionyl L-carnitine and acetyl L-carnitine is any salt of these compounds with an acid that does not give rise to unwanted toxic or side effects.

Such acids are well known to pharmacologists and to experts in pharmaceutical technology.

Examples of such salts, though not exclusively these, are, for example, chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucose phosphate, tartrate, acid tartrate, magnesium tartrate, 2-amino-ethane sulphonate, magnesium 2-amino-ethane sulphonate, choline tartrate and trichloroacetate.

Propionyl L-carnitine and acetyl L-carnitine can be in any form suitable for oral or parenteral administration to human subjects.

Propionyl L-carnitine and acetyl L-carnitine can be formulated together, as a mixture, or can be formulated separately (separate packs), using known methods. Propionyl L-carnitine and acetyl L-carnitine can be administered to an individual both when contained in a mixture and when packaged separately.

On the basis of various factors, such as the concentration of the active ingredients or the patient's condition, the combination according to the invention can be marketed as a health food supplement, nutritional supplement, or therapeutic product on sale with or without a compulsory prescription.

The preparation of the combination according to the present invention, when in unit dosage form, contains from 4.0 to 0.5 g of propionyl L-carnitine inner salt, and from 0.50 g to 4.0 g of acetyl L-carnitine inner salt, or an equimolar amount of one of their pharmaceutically acceptable salts.

The preferred preparation of the combination, in unit dosage form, contains 2 g of propionyl L-carnitine inner salt, and 2 g of acetyl L-carnitine inner salt, or an equimolar amount of one of their pharmaceutically acceptable salts.

It has been found, however, that, although the daily dose of the above-mentioned active ingredients to be administered depends on the patient's age, weight and condition, using professional experience, it is generally advisable to administer, in a single or in multiple doses, from approximately 0.5 to 4.0 g/day of propionyl L-carnitine, and from 4.0 to 0.5 g/day of acetyl L-carnitine, or an equimolar amount of one of their pharmaceutically acceptable salts.

Larger doses can be administered thanks to the extremely low toxicity of said active ingredients.

Reported here below is a clinical trial conducted in order to evaluate the activity of the combination according to the association in the treatment of the symptoms of male ageing.

The determinations carried out during the clinical trial were aimed at assessing any pathological changes affecting the cervico-urethral district and the efficacy of the compound according to the invention as compared to the reference compound.

The patients recruited into the trial had to match up to the following inclusion/exclusion criteria.

Inclusion Criteria

Patients aged over 60 years with lowered blood concentrations of free and total testosterone (*The Aging Male*, 4: 151-162, 2001) and complaining of symptoms figuring in the working definition of andropause proposed by the International Society for the Study of the Aging Male (I.S.S.A.M.) (*The Aging Male*, 4: 151-162, 2001): reduced libido or sex drive and erectile function, depressed mood, difficulty concentrating, irritability and fatigue.

Exclusion Criteria

Obstruction or inflammation of the lower urinary tract; prostate volume >20 $cm^3$ at suprapubic ultrasonography; increased concentration of prostate-specific antigen (PSA); increased suspicion regarding prostate consistency at rectal exploration (*Am. J. Med.*, 110: 563-571, 2001); heavy smokers and drinkers; recent myocardial infarct (<6 months); diabetes; hypertension or other untreated cardiovascular diseases; active cancer; use of psychotropic drugs or anticancer therapy; recent major surgery (<6 months); increased prolactinaemia.

In all, 57 patients were included, 12 of whom failed to complete the trial.

The results obtained, reported here below, refer to 45 patients with a mean age of 66 years (range: 60-74).

The patients were divided at random into 3 groups of 15 each. The patients in the first group were administered testosterone undecanoate (Andriol$^R$-Organon) 40×2 mg/day, while those in the second group received propionyl L-carnitine 1+1 g/day associated with acetyl L-carnitine 1+1 g/day, and those in the third group vitamin C (Redoxon$^R$-Roche) 500 mg/day as a placebo.

The above-mentioned compounds were presented to the patients in anonymous containers and administered for 6 months.

Data Collection

Medical history-taking and physical examinations were done for all patients. The following data were also collected prior to the start of treatment, after 3 months of treatment and at the end of the treatment period (6 months):

1. Total blood prostate-specific antigen (PSA) (ng/ml) as measured with the automatic test and monoclonal antibodies [Rigatti P., Scattoni V., *PSA: Antigene prostatico specifico. Edizioni Medico Scientifiche (EDIMES) Pavia*, 1997].

2. Prostate volume ($cm^3$) as measured by suprapubic ultrasonography and calculated by means of the three diameters rule [Rigatti P., Scattoni V., *PSA: Antigene prostatico specifico. Edizioni Medico Scientifiche (EDIMES) Pavia*, 1997].

3. Peak systolic volume (PSV) (cm/sec), end-diastolic velocity (EDV) (cm/sec), and Resistance Index (RI) (%) of the penile arteries (right and left cavernous e dorsal) as measured by means of penile basal and dynamic colour Doppler ultrasonography. RI was calculated as follows: (PSV−EDV/EDV)×100 (*Urology*, 1997: 49: 822-830).

4. Duration of full erections (in minutes) in the course of a recording period of three nights performed with Rigiscan. What is meant by full erection is an increase in rigidity greater than 70% above the basal line and an increase in diameter >2 cm at the head and >3 cm at the base (Eardly I, Sethia K., *Erectile Dysfunction Current Management and Treatment*. The Mosby Company, London 1998).

5. Free and total blood testosterone, LH and prolactin levels (*The Aging Male*, 4: 151-162, 2001).

6. Sexual function was checked by means of semistructured interviews and administration of the International Index of Erectile Function (IIEF-15) (*Urology*, 1997:49: 822-830). A score was calculated for each patient.

7. Depression was quantified by means of the Hamilton Depression Scale questionnaire (DMS III) (*Cancer*, 94: 2481-2489, 2002). A score was calculated for each patient.

8. The subjective sensation of fatigue was calculated using the fatigue scale (Lison L.: *Statistica applicata alla biologia sperimentale. Milano: Casa Editrice Ambrosiana*, 1972). A score was calculated for each patient.

9. Side effects.

Blood concentrations of PSA, free and total testosterone, prolactin LH, prostate volume, PSV, EDV, RI, full erection duration, IIEF-15, DMS III, and fatigue scale scores were compared between and within groups by means of 3×3 factorial analysis of variance for randomised blocks (1 patient=1 block). Comparison of the mean values was done on the raw data with the exclusion of RI which used data subjected to angular transformation ($sin^{-1} \sqrt{P/100}$) for the comparisons. Side effects were compared using the chi-square test (Lison L.: *Statistica applicata alla biologia sperimentale. Milano: Casa Editrice Ambrosiana*, 1972). The results obtained are given in the following examples.

EXAMPLE 1

Table 1 shows the mean PSA levels in the three patient groups before, during and after therapy with the combination according to the invention, with the reference compound (testosterone) and with a placebo.

The results obtained, presented in Table 1, show that the treatment with the compounds tested induced no significant changes.

TABLE 1

Mean serum levels of total prostate-specific antigen (PSA) ng/ml before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | PSA ng/ml |
|---|---|---|
| Testosterone undecanoate | Before therapy | 2.02 ± 0.74 |
| 40 × 2 mg/day | During therapy (3 mos) | 2.01 ± 0.79 |
|  | After therapy (6 mos) | 2.02 ± 0.85 |
| Propionyl L-carnitine | Before therapy | 2.36 ± 0.87 |
| 1 × 2 g/day + | During therapy (3 mos) | 2.21 ± 0.654 |
| acetyl L-carnitine |  |  |
| 1 × 2 g/day | After therapy (6 mos) | 2.33 ± 0.77 |
| Placebo | Before therapy | 1.80 ± 0.77 |
|  | During therapy (3 months) | 1.75 ± 0.75 |
|  | After therapy (6 mos) | 1.75 ± 0.75 |

These results indicate that the treatment with testosterone, with the combination according to the invention and with placebo did not significantly increase blood PSA levels.

EXAMPLE 2

Table 2 presents the data for mean prostate volume values before, during and after therapy with testosterone, with the combination according to the invention and with placebo.

TABLE 2

Mean prostate volume ($cm^3$) as measured by suprapubic ultrasonography and calculation of the three diameters, before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Prostate volume ($cm^3$) |
|---|---|---|
| Testosterone | Before therapy | 15.3 ± 2.8 |
| undecanoate | During therapy (3 mos) | 15.5 ± 3.0 |
| 40 × 2 mg/day |  |  |
|  | After therapy (6 mos) | 15.5 ± 2.6 |
| Propionyl L-carnitine 1 × | Before therapy | 15.2 ± 2.7 |
| 2 g/day + acetyl L- | During therapy (3 mos) | 14.5 ± 2.6 |
| carnitine 1 × 2 g/day |  |  |
|  | After therapy (6 mos) | 15.1 ± 3.1 |
| Placebo | Before therapy | 15.6 ± 3.2 |
|  | During therapy (3 mos) | 15.5 ± 3.4 |
|  | After therapy (6 mos) | 15.6 ± 3.3 |

The results presented in Table 2 indicate that the treatment with the compounds tested did not significantly increase prostate volume.

EXAMPLES 3 AND 4

Table 3 presents the data for peak systolic velocity (PSV) of the right cavernous artery of the penis before, during and after therapy with the combination according to the invention, with testosterone and with placebo.

TABLE 3

Peak systolic velocity (PSV) (mean value in cm/sec) of the right cavernous artery of the penis as measured by dynamic colour Doppler ultrasonography before, during and after administration of testosterone undecanoate (40 × 2 mg/day), propionyl L-carnitine 1 × 2 g/day +acetyl L-carnitine 1 × 2 g/day or placebo for 6 months to three groups of 15 patients each. Data are mean ± standard deviation.

| Type of therapy | Observation time | Right cavernous artery PSV (cm/sec) |
|---|---|---|
| Testosterone undecanoate 40 × 2 mg/day | Before therapy | 33.2 ± 3.9 |
| | During therapy (3 mos) | 32.8 ± 4.2 |
| | After therapy (6 mos) | 33.7 ± 3.7 |
| Propionyl L-carnitine 1 × 2 g/day + acetyl L-carnitine 1 × 2 g/day | Before therapy | 33.9 ± 3.2 |
| | During therapy (3 mos) | 33.9 ± 3.2 |
| | After therapy (6 mos) | 33.9 ± 3.3 |
| Placebo | Before therapy | 33.7 ± 4.3 |
| | During therapy (3 mos) | 33.9 ± 5.0 |
| | After therapy (6 mos) | 33.8 ± 4.7 |

The results presented in Table 3 indicate that the treatment with the compounds tested did not induce significant changes.

Similar results emerged on measuring the PSV of the left cavernous artery; the results obtained, presented in Table 4, show, in fact, that the treatment did not induce any significant changes.

TABLE 4

Peak systolic velocity (PSV) (mean value in cm/sec) of the left cavernous artery of the penis as measured by dynamic colour Doppler ultrasonography before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Left cavernous PSV (cm/sec) |
|---|---|---|
| Testosterone undecanoate 40 × 2 mg/day | Before therapy | 33.6 ± 3.7 |
| | During therapy (3 mos) | 32.6 ± 4.2 |
| | After therapy (6 mos) | 33.5 ± 3.5 |
| Propionyl L-carnitine 1 × 2 g/day + acetyl L-carnitine 1 × 2 g/day | Before therapy | 34.1 ± 3.3 |
| | During therapy (3 mos) | 34.2 ± 3.3 |
| | After therapy (6 mos) | 34.1 ± 3.5 |
| Placebo | Before therapy | 33.4 ± 4.0 |
| | During therapy (3 mos) | 32.5 ± 4.8 |
| | After therapy (6 mos) | 32.7 ± 4.9 |

EXAMPLES 5, 6, 7 AND 8

The results presented in Tables 5, 6, 7 and 8 here below show that the treatments administered also induced no significant differences either in the case of the other vascular parameters (EDV and RI) or as affecting the right or left cavernous arteries.

TABLE 5

End-diastolic velocity (EDV) (mean value in cm/sec) of the right cavernous artery of the penis as measured by dynamic colour Doppler ultrasonography before, during and after administration of testosterone undecanoate (40 × 2 mg/day), propionyl L-carnitine 1 × 2 g/day +acetyl L-carnitine 1 × 2 g/day or placebo for 6 months to three groups of 15 patients each. Data are mean ± standard deviation.

| Type of therapy | Observation time | Right cavernous artery EDV (cm/sec) |
|---|---|---|
| Testosterone undecanoate 40 × 2 mg/day | Before therapy | 7.8 ± 3.6 |
| | During therapy (3 mos) | 7.9 ± 3.6 |
| | After therapy (6 mos) | 7.9 ± 3.6 |
| Propionyl L-carnitine 1 × 2 g/day + acetyl L-carnitine 1 × 2 g/day | Before therapy | 6.8 ± 3.6 |
| | During therapy (3 mos) | 7.1 ± 3.8 |
| | After therapy (6 mos) | 6.9 ± 3.6 |
| Placebo | Before therapy | 6.5 ± 3.8 |
| | During therapy (3 mos) | 6.7 ± 4.0 |
| | After therapy (6 mos) | 6.7 ± 4.3 |

TABLE 6

End-diastolic veloicity (EDV) (mean value in cm/sec) of the left cavernous artery of the penis as measured by dynamic color Doppler ultrasonography before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Left cavernous artery EDV (cm/sec) |
|---|---|---|
| Testosterone undecanoate 40 × 2 mg/day | Before therapy | 7.7 ± 3.5 |
| | During therapy (3 mos) | 7.5 ± 3.3 |
| | After therapy (6 mos) | 7.4 ± 3.3 |
| Propionyl L-carnitine 1 × 2 g/day + acetyl L-carnitine 1 × 2 g/day | Before therapy | 6.4 ± 3.6 |
| | During therapy (3 mos) | 6.4 ± 3.3 |
| | After therapy (6 mos) | 6.5 ± 3.2 |
| Placebo | Before therapy | 6.9 ± 3.8 |
| | During therapy (3 mos) | 6.3 ± 3.8 |
| | After therapy (6 mos) | 6.2 ± 3.8 |

TABLE 7

Resistance Index (RI) (%) of right cavernous artery before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data used were values subjected to angular transformation ($\sin^{-1} \sqrt{P/100}$) and presented as mean ± standard deviation.

| Type of therapy | Observation time | Right cavernous artery RI % |
|---|---|---|
| Testosterone undecanoate 40 × 2 mg/day | Before therapy | 64.6 ± 8.4 |
| | During therapy (3 mos) | 60.9 ± 8.4 |
| | After therapy (6 mos) | 61.1 ± 7.9 |
| Propionyl L-carnitine 1 × 2 g/day + acetyl L-carnitine 1 × 2 g/day | Before therapy | 64.2 ± 7.4 |
| | During therapy (3 mos) | 63.7 ± 7.4 |
| | After therapy (6 mos) | 64.1 ± 7.3 |
| Placebo | Before therapy | 64.5 ± 8.8 |
| | During therapy (3 mos) | 64.4 ± 9.2 |
| | After therapy (6 mos) | 64.7 ± 9.9 |

TABLE 8

Resistance Index (RI) (%) of left cavernous artery before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data used were values submitted to angular transformation ($\sin^{-1} \sqrt{P/100}$) and presented as means ± standard deviation.

| Type of therapy | Observation time | Left cavernous artery RI % |
|---|---|---|
| Testosterone undecanoate 40 × 2 mg/day | Before therapy | 61.5 ± 8.3 |
| | Durino therapy (3 mos) | 61.5 ± 7.8 |
| | After therapy (6 mos) | 62.1 ± 7.0 |
| Propionyl L-carnitine 1 × 2 g/day + acetyl L-carnitine 1 × 2 g/day | Before therapy | 64.8 ± 6.8 |
| | During therapy (3 mos) | 64.9 ± 7.0 |
| | After therapy (6 mos) | 64.7 ± 7.0 |
| Placebo | Before therapy | 63.3 ± 8.7 |
| | During therapy (3 mos) | 64.6 ± 9.6 |
| | After therapy (6 mos) | 64.7 ± 8.7 |

EXAMPLE 9

Table 9 presents the data for duration of full nocturnal erections in minutes recorded by Rigiscan for a period of 3 nights before, during and after therapy with the combination according to the invention, with testosterone and with placebo. The combination according to the invention induced a significant increase in duration of full nocturnal erections both at 3 ($F=11.6$; $P<0.01$) and at 6 months ($F=19.1$; $P<0.01$), while the administration of testosterone induced a significant increase in duration of full nocturnal erections at 6 months ($F=12.4$, $P<0.01$), but not at 3 months ($F=1.01$; $P=n.s.$).

In addition, the duration of the nocturnal erections was greater after 6 months in the group treated with the combination according to the invention ($F=4.2$, $P<0.05$) than that of those observed after 6 months in the group treated with testosterone. The administration of placebo had no effect on the duration of full nocturnal erections ($F=2.4$, $P=n.s.$).

TABLE 9

Duration of full erections (in minutes) in the course of a recording period of three nights by Rigiscan before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Duration of full erections (in minutes) |
|---|---|---|
| Testosterone undecanoate 40 × 2 mg/day | Before therapy | 108.3 ± 18.7 |
| | During therapy (3 mos) | 112.7 ± 21.1 |
| | After therapy (6 mos) | 119.6 ± 26.0 |
| Propionyl L-carnitine 1 × 2 g/day + acetyl L-carnitine 1 × 2 g/day | Before therapy | 98.9 ± 18.5 |
| | During therapy (3 mos) | 112.8 ± 16.1 |
| | After therapy (6 mos) | 136.9 ± 28.1 |
| Placebo | Before therapy | 105.3 ± 21.2 |
| | During therapy (3 mos) | 107.7 ± 21.2 |
| | After therapy (6 mos) | 102.6 ± 22.9 |

These results indicate that the combination according to the invention is significantly more active than testosterone in increasing nocturnal erections (by means of a non-psychological and non-macrovascular organic mechanism).

EXAMPLE 10 AND 11

Table 10 presents the data for blood total testosterone levels before, during and after therapy with the combination according to the invention, with testosterone and with placebo. The treatment with the compounds tested induced no significant changes.

In particular, administration of the combination according to the invention, of testosterone and of placebo induced no significant increases in total serum testosterone at either 3 or 6 months.

TABLE 10

Blood levels of total testosterone before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean + standard deviation.

| Type of therapy | Observation time | Total testosterone nmol/l |
|---|---|---|
| Testosterone undecanoate 40 × 2 mg/day | Before therapy | 14.5 ± 2.1 |
| | During therapy (3 mos) | 15.5 ± 3.9 |
| | After therapy (6 mos) | 15.8 ± 2.6 |
| Propionyl L-carnitine 1 × 2 g/day + acetyl L-carnitine 1 × 2 g/day | Before therapy | 15.9 ± 2.8 |
| | During therapy (3 mos) | 15.2 ± 3.0 |
| | After therapy (6 mos) | 15.8 ± 4.4 |
| Placebo | Before therapy | 14.9 ± 2.0 |
| | During therapy (3 mos) | 14.8 ± 2.3 |
| | After therapy (6 mos) | 14.9 ± 1.9 |

These results indicate that the activity of oral testosterone is exerted mainly through an increase in free and total blood testosterone, whereas the compound according to the invention acts in a different way, probably through restoration of the physiological concentration of ROS.

Very similar results were obtained on analysing free blood testosterone during treatment with the compounds tested. The results obtained are presented in Table 11.

TABLE 11

Blood levels of free testosterone before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Free blood testosterone pg/ml |
|---|---|---|
| Testosterone undecanoate 40 × 2 mg/day | Before therapy | 4.4 ± 0.8 |
| | During therapy (3 mos) | 19.5 ± 4.2 |
| | After therapy (6 mos) | 19.7 ± 4.0 |
| Propionyl L-carnitine 1 × 2 g/day + acetyl L-carnitine 1 × 2 g/day | Before therapy | 4.6 ± 1.0 |
| | During therapy (3 mos) | 4.5 ± 1.1 |
| | After therapy (6 mos) | 4.5 ± 0.8 |
| Placebo | Before therapy | 4.2 ± 0.6 |
| | During therapy (3 mos) | 4.3 ± 0.8 |
| | After therapy (6 mos) | 4.1 ± 0.7 |

EXAMPLE 12

Table 12 presents the data for blood levels of LH before, during and after treatment with the combination according to the invention, with testosterone and with placebo.

In particular, treatment with the combination according to the invention and with placebo induced no significant changes in LH either at 3 or at 6 months (F<1, P=n.s.). In contrast, the administration of testosterone led to a statistically significant reduction in blood levels of LH at 3 months (F=229 P<0.01), and a significant reduction at 6 months.

TABLE 12

Blood levels of LH before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | LH IU/1 |
|---|---|---|
| Testosterone undecanoate 40 × 2 mg/day | Before therapy | 8.9 ± 0.6 |
| | During therapy (3 mos) | 4.3 ± 0.6 |
| | After therapy (6 mos) | 4.2 ± 1.2 |
| Propionyl L-carnitine 1 × 2 g/day + acetyl L-carnitine 1 × 2 g/day | Before therapy | 8.4 ± 0.9 |
| | During therapy (3 mos) | 8.5 ± 0.7 |
| | After therapy (6 mos) | 8.5 ± 0.8 |
| Placebo | Before therapy | 8.7 ± 0.6 |
| | During therapy (3 mos) | 8.6 ± 0.6 |
| | After therapy (6 mos) | 8.7 ± 0.5 |

These results confirm that it is the rise in free blood testosterone that causes the activity of testosterone in resolving the symptoms associated with ageing.

EXAMPLE 13

Table 13 presents the data for blood prolactin levels before, during and after treatment with the combination according to the invention, with testosterone and with placebo. The results obtained show that the treatment did not induce any significant changes.

TABLE 13

Blood prolactin levels before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Prolactin µg/ml |
| --- | --- | --- |
| Testosterone undecanoate 40 × 2 mg/day | Before therapy | 7.7 ± 1.6 |
| | During therapy (3 mos) | 7.4 ± 1.7 |
| | After therapy (6 mos) | 7.3 ± 1.8 |
| Propionyl L-carnitine 1 × 2 g/day + acetyl L-carnitine 1 × 2 g/day | Before therapy | 7.6 ± 1.9 |
| | During therapy (3 mos) | 7.4 ± 1.9 |
| | After therapy (6 mos) | 7.5 ± 2.2 |
| Placebo | Before therapy | 7.4 ± 1.7 |
| | During therapy (3 mos) | 7.7 ± 1.7 |
| | After therapy (6 mos) | 7.3 ± 1.8 |

These results indicate that oral testosterone and the combination according to the invention are capable of increasing libido regardless of prolactin (a hormone an increase in which gives rise to a reduction of libido and vice versa).

EXAMPLE 14

Table 14 presents the scores on the International Index of Erectile Function questionnaire (IIEF-15)—"Erectile Function" section, before, during and after therapy with the combination according to the invention, with testosterone and with placebo. The combination according to the invention and testosterone induced a significant increase in scores both at 3 months ($F=31.5$, $P<0.01$ and $F=6.3$, $P<0.05$, respectively) and at 6 months ($F=18.9$, $P<0.01$ and $F=29.2$, $P<0.01$, respectively). Administration of the placebo induced no significant changes in scores.

TABLE 14

Scores on the International Index of Erectile Function questionnaire (LIEF-15)—"Erectile Function" section, before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Score |
| --- | --- | --- |
| Testosterone undecanoate 40 × 2 mg/day | Before therapy | 13.8 ± 2.7 |
| | During therapy (3 mos) | 16.7 ± 3.7 |
| | After therapy (6 mos) | 20.2 ± 5.3 |
| Propionyl L-carnitine 1 × 2 g/day + acetyl L-carnitine 1 × 2 g/day | Before therapy | 11.4 ± 5.4 |
| | During therapy (3 mos) | 16.7 ± 5.4 |
| | After therapy (6 mos) | 21.9 ± 7.3 |
| Placebo | Before therapy | 13.8 ± 1.1 |
| | During therapy (3 mos) | 12.9 ± 2.0 |
| | After therapy (6 mos) | 14.2 ± 2.9 |

These results indicate that the combination according to the invention and oral testosterone significantly increase erectile activity, whereas the placebo proves inactive.

EXAMPLES 15 AND 16

Very similar results were obtained in the "Intercourse Satisfaction" (Table 15) and "Sexual Desire" sections (Table 16).

These results, too, indicate that the combination according to the invention and oral testosterone significantly increased intercourse satisfaction and sexual desire.

TABLE 15

Scores on the International Index of Erectile Function questionnaire (LIEF-15)—"Intercourse Satisfaction" section, before, during and after administration of testosterone undecanoate (40 × 2 mg/day), propionyl L-carnitine 1 × 2 g/day + acetyl L-carnitine 1 × 2 g/day or placebo for 6 months to three groups of 15 patients. Data are mean ± standard deviation.

| Type of therapy | Observation time | Score |
| --- | --- | --- |
| Testosterone undecanoate 40 × 2 mg/day | Before therapy | 4.1 ± 0.8 |
| | During therapy (3 mos) | 4.8 ± 0.8 |
| | After therapy (6 mos) | 5.8 ± 1.9 |
| Propionyl L-carnitine 1 × 2 g/day + acetyl L-carnitine 1 × 2 g/day | Before therapy | 4.6 ± 1.0 |
| | During therapy (3 mos) | 5.3 ± 1.2 |
| | After therapy (6 mos) | 6.9 ± 2.5 |
| Placebo | Before therapy | 3.9 ± 0.8 |
| | During therapy (3 mos) | 4.3 ± 0.8 |
| | After therapy (6 mos) | 4.1 ± 0.7 |

TABLE 16

Scores on the International Index of Erectile Function questionnaire (IIEF-15)—"Sexual Desire" section, before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. The data are means ± standard deviation.

| Type of therapy | Observation time | Score |
| --- | --- | --- |
| Testosterone undecanoate 40 × 2 mg/day | Before therapy | 4.3 ± 1.0 |
| | During therapy (3 mos) | 5.7 ± 0.8 |
| | After therapy (6 mos) | 7.1 ± 0.9 |
| Propionyl L-carnitine 1 × 2 g/day + acetyl L-carnitine 1× 2 g/day | Before therapy | 3.9 ± 0.8 |
| | During therapy (3 mos) | 6.6 ± 1.3 |
| | After therapy (6 mos) | 7.3 ± 1.9 |
| Placebo | Before therapy | 3.3 ± 0.9 |
| | During therapy (3 mos) | 3.3 ± 0.9 |
| | After therapy (6 mos) | 3.5 ± 0.5 |

EXAMPLE 17

Table 17 presents the scores on the International Index of Erectile Function questionnaire (IIEF-15)—"General Satisfaction" section, before, during and after therapy with the combination according to the invention, with testosterone and with placebo. The treatment induced significant changes; in particular, the combination according to the invention significantly increased the scores at 3 months ($F=33.3$ $P<0.01$) and at 6 months ($F=33.6$, $P<0.01$). The administration of testosterone and placebo failed to induce any significant changes in scores.

TABLE 17

Scores on the International Index of Erectile Function questionnaire (IIEF-15)—"Orgasmic Function" section, before, during and after administration of testosterone undecanoate (40 × 2 mg/day), propionyl L-carnitine 1 × 2 g/day + acetyl L-carnitine 1 × 2 g/day or placebo for 6 months to three groups of 15 patients each. Data are mean ± standard deviation.

| Type of therapy | Observation time | Score |
| --- | --- | --- |
| Testosterone undecanoate 40 × 2 mg/day | Before therapy | 3.2 ± 1.2 |
| | During therapy (3 mos) | 3.9 ± 0.9 |
| | After therapy (6 mos) | 4.7 ± 1.8 |

TABLE 17-continued

Scores on the International Index of Erectile Function questionnaire
(IIEF-15)—"Orgasmic Function" section, before, during and after
administration of testosterone undecanoate (40 × 2 mg/day), propionyl
L-carnitine 1 × 2 g/day + acetyl L-carnitine 1 × 2 g/day or placebo for 6
months to three groups of 15
patients each. Data are mean ± standard deviation.

| Type of therapy | Observation time | Score |
|---|---|---|
| Propionyl L-carnitine 1 × 2 | Before therapy | 3.7 ± 1.1 |
| g/day + | During therapy | 5.4 ± 1.3 |
| acetyl L-carnitine | (3 mos) | |
| 1 × 2 g/day | After therapy (6 mos) | 7.2 ± 1.1 |
| Placebo | Before therapy | 2.9 ± 0.7 |
| | During therapy | 3.4 ± 1.6 |
| | (3 mos) | |
| | After therapy (6 mos) | 3.0 ± 0.6 |

These results indicate that the combination according to the invention is significantly more active than testosterone and placebo in increasing the general well-being (coenaesthesia) of patients receiving the therapy.

EXAMPLE 18

Table 18 presents the scores on the International Index of Erectile Function questionnaire (IIEF-15)—"Orgasmic Function" section, before, during and after therapy with the combination according to the invention, with testosterone and with placebo. The combination according to the invention significantly increased the scores at 3 months (F=33.6, P<0.01) and 6 months (F=21, P<0.01). The administration of testosterone significantly increased the scores at 3 months (F=12.6, P<0.01) but not at 6 months (F=2.3, P=n.s.). The placebo did not induce any significant changes in score.

TABLE 18

Scores on the International Index of Erectile Function questionnaire
(IIEF-15)—"General Satisfaction" section, before, during and after
administration of testosterone undecanoate (40 × 2 mg/day),
propionyl L-carnitine 1 × 2 g/day + acetyl L-carnitine 1 × 2 g/day
or placebo for 6 months to three groups of 15
patients each. Data are mean ± standard deviation.

| Type of therapy | Observation time | Score |
|---|---|---|
| Testosterone undecanoate | Before therapy | 3.2 ± 0.6 |
| 40 × 2 mg/day | During therapy | 3.7 ± 1.1 |
| | (3 mos) | |
| | After therapy (6 mos) | 4.4 ± 2.2 |
| Propionyl L-carnitine 1 × 2 | Before therapy | 3.1 ± 0.6 |
| g/day + | During therapy | 5.2 ± 1.5 |
| acetyl L-carnitine | (3 mos) | |
| 1 × 2 g/day | After therapy (6 mos) | 7.1 ± 1.8 |
| Placebo | Before therapy | 2.8 ± 0.7 |
| | During therapy | 2.9 ± 0.5 |
| | (3 mos) | |
| | After therapy (6 mos) | 3.1 ± 0.8 |

These results indicate that testosterone and the combination according to the invention are significantly more active than placebo in increasing the general satisfaction of patients receiving the treatment. In particular, the combination according to the invention proved significantly more active than testosterone.

EXAMPLE 19

Table 19 presents the scores on the DMS III questionnaire before, during and after therapy with the combination according to the invention, with testosterone and with placebo. The combination according to the invention induced a significant decrease in DMS III scores both at 3 months (F=19.2; P<0.01) and 6 months (F=13.0; P<0.01). The administration of testosterone induced a significant decrease in DMS III scores at 3 months (F=4.07; P<0.05), but not at 6 months (F=2.5; P=n.s.). The administration of placebo induced a significant decrease in DMS III scores at 3 months (F=7.75; P<0.05), but not at 6 months (F=1; P=n.s.). No significant difference was detected between the scores obtained at 6 months with placebo and testosterone (F<1, P=n.s.), whereas the score obtained with the combination according to the invention was significantly lower (F=17.4; P<0.01).

TABLE 19

Scores on the Hamilton Depression Scale questionnaire (DMS HI)
before, during and after administration
of testosterone undecanoate (40 × 2 mg/day), propionyl
L-carnitine 1 × 2 g/day + acetyl L-carnitine 1 × 2 g/day
or placebo for 6 months to three groups of 15 patients each.
Data are mean ± standard deviation.

| Type of therapy | Observation time | Score |
|---|---|---|
| Testosterone undecanoate | Before therapy | 6.6 ± 0 |
| 40 × 2 mg/day | During therapy | 5.8 ± 0.7 |
| | (3 mos) | |
| | After therapy (6 mos) | 5.1 ± 1.3 |
| Propionyl L-carnitine 1 × 2 | Before therapy | 6.3 ± 1.1 |
| g/day + | During therapy | 4.7 ± 0.9 |
| acetyl L-carnitine | (3 mos) | |
| 1 × 2 g/day | After therapy (6 mos) | 3.2 ± 1.1 |
| Placebo | Before therapy | 6.8 ± 0.8 |
| | During therapy (3 mos) | 5.8 ± 0.7 |
| | After therapy (6 mos) | 5.5 ± 1.1 |

These results indicate that the combination according to the invention is significantly more active than testosterone and placebo (which exhibit similar activity) in improving the mood of subjects receiving the treatment.

EXAMPLE 20

Table 20 presents the scores on the fatigue scale questionnaire before, during and after therapy with the combination according to the invention, with testosterone and with placebo. The combination according to the invention induced a statistically significant increase in the scores at 3 months (F=12.2, P<0.01) and at 6 months (F=9.3, P<0.01).

The administration of testosterone induced a statistically significant increase in the score at 3 months (F=33.6, P<0.01) but no significant increase at 6 months (F=5.9, P=n.s.). Placebo induced no significant changes in score.

TABLE 20

Scores on the fatigue scale before, during and after administration
of testosterone undecanoate (40 × 2 mg/day),
propionyl L-carnitine 1 × 2 g/day + acetyl L-carnitine
1 × 2 g/day or placebo for 6 months to
three groups of 15 patients each. Data are mean ± standard deviation.

| Type of therapy | Observation time | Score |
|---|---|---|
| Testosterone undecanoate | Before therapy | 2.8 ± 1.3 |
| 40 × 2 mg/day | During therapy | 1.1 ± 1.0 |
| | (3 mos) | |
| | After therapy (6 mos) | 0.6 ± 0.4 |
| Propionyl L-carnitine 1 × 2 | Before therapy | 2.7 ± 1.3 |
| g/day + acetyl L-carnitine | During therapy (3 mos) | 1.3 ± 1.1 |
| 1 × 2 g/day | After therapy (6 mos) | 0.5 ± 0.4 |
| Placebo | Before therapy | 2.9 ± 0.8 |
| | During therapy | 2.9 ± 0.8 |
| | (3 mos) | |
| | After therapy (6 mos) | 3.0 ± 0.8 |

The results presented in Table 20 indicate that testosterone and the combination according to the invention are significantly more active than placebo in increasing the sensation of general well-being in the patients treated. The best results were achieved with the compound according to the invention.

Unlike placebo, both testosterone and the combination according to the invention proved capable of attenuating the symptoms of andropause.

Neither of the compounds tested induced pathological changes affecting the cervico-urethral district. In any event, for testosterone, as mentioned above, its use is still contraindicated in the case of disease of the prostate district as well as for the onset of troublesome adverse effects on the liver, on lipid status, on cardiovascular and prostate diseases, and on sleep and behavioural disorders.

It should be stressed that an important proportion of patients above 50 years of age suffer from diseases of the cervico-urethral district, and therefore cannot be treated with testosterone (see Exclusion criteria).

The combination according to the invention may therefore be regarded as the drug of choice in the treatment of patients with symptoms associated with ageing, since, in addition to being more active than testosterone, it can be used in a larger number of patients.

The invention claimed is:

1. A method of treating erectile dysfunction caused by andropause by administering to a subject in need thereof an effective amount of propionyl L-carnitine in combination with acetyl L-carnitine or one of their pharmaceutically acceptable salts the improvement comprising the lack of increase of blood testosterone levels.

2. The method according to claim 1, in which the andropause is caused by aging.

3. The method according to claim 1, in which the andropause is caused by chemical or surgical castration.

4. The method according to claim 1, in which the pharmaceutically acceptable salt is selected from the group consisting of: chloride, bromide, orotate, acid aspartate, acid citrate, magnesium citrate, acid phosphate, fumarate and acid fumarate, magnesium fumarate, lactate, maleate and acid maleate, mucate, acid oxalate, pamoate, acid pamoate, acid sulphate, glucose phosphate, glucose phosphate, tartrate, acid tartrate, magnesium tartrate, 2-aminoethane sulphonate, magnesium 2-aminoethane sulphonate, choline tartrate and trichloroacetate.

5. The method according to claim 1, in which propionyl L-carnitine in combination with acetyl L-carnitine are in a unit dosage form containing from 4.0 g to 0.50 g of propionyl L-carnitine inner salt, and from 0.50 g to 4.0 g of acetyl L-carnitine inner salt or an equimolar amount of one of their pharmaceutically acceptable salts.

6. The method according to claim 5, in unit dose form containing 2 g of propionyl L-carnitine inner salt and 2 g of acetyl L-carnitine inner salt, or an equimolar amount of one of their pharmaceutically acceptable salts.

7. The method according to claim 5, in which propionyl L-carnitine in combination with acetyl L-carnitine are formulated together, as a mixture, or are formulated separately.

8. The method of claim 7, in which propionyl L-carnitine in combination with acetyl L-carnitine are in a form suitable for oral or parenteral administration.

* * * * *